United States Patent
Franz et al.

(10) Patent No.: US 7,766,858 B2
(45) Date of Patent: Aug. 3, 2010

(54) PORTABLE HAND-OPERABLE DEVICE FOR APPLYING PNEUMATIC PRESSURE PULSES TO AN EAR CANAL

(75) Inventors: Burkhard Franz, Wantirna (AU); Richard Michael Stephens, Lower Plenty (AU); Christopher Leslie Peters, Donvale (AU)

(73) Assignee: Burkhard Franz Pty. Ltd., Victoria (AU)

( * ) Notice: Subject to any disclaimer, the term of this patent is extended or adjusted under 35 U.S.C. 154(b) by 1013 days.

(21) Appl. No.: 10/557,167

(22) PCT Filed: May 19, 2004

(86) PCT No.: PCT/AU2004/000655

§ 371 (c)(1),
(2), (4) Date: Aug. 24, 2006

(87) PCT Pub. No.: WO2004/100844

PCT Pub. Date: Nov. 25, 2004

(65) Prior Publication Data

US 2007/0060948 A1    Mar. 15, 2007

(30) Foreign Application Priority Data

May 19, 2003    (AU)    ............... 2003902425

(51) Int. Cl.
*A61M 37/00*    (2006.01)
(52) U.S. Cl. ...................................... 604/26
(58) Field of Classification Search ............ 601/76, 601/77, 10; 600/559; 607/105; 604/26
See application file for complete search history.

(56) References Cited

U.S. PATENT DOCUMENTS

| | | | |
|---|---|---|---|
| 2,176,366 A | | 10/1939 | Smith |
| 3,921,977 A | * | 11/1975 | Brink ............................ 222/4 |
| 4,754,748 A | | 7/1988 | Antowski |
| 5,746,725 A | | 5/1998 | Shalon et al. |
| 6,159,171 A | * | 12/2000 | Densert et al. ................ 601/76 |
| 6,629,938 B1 | | 10/2003 | Engvall et al. |
| 2002/0069883 A1 | | 6/2002 | Hirchenbain |

FOREIGN PATENT DOCUMENTS

DE    493956    3/1930

(Continued)

*Primary Examiner*—Manuel A Mendez
(74) *Attorney, Agent, or Firm*—Kirk Hahn

(57) ABSTRACT

A hand-held device (10) for creating a pressure change in a person's ear canal. It has an interior space forming an air chamber (50), a plunger (58) and a valve means (52) frictionally engaged with said plunger (58), a tube (14) with an earpiece (48), and a finger-actuated diaphragm (60) in an external wall of the air chamber (50). The diaphragm (60) moves the plunger (58) from a resting position, and in a first direction. A spring (56) returns the diaphragm (60) to its undepressed position. Initial movement of the plunger (58) in said first direction from said resting position displaces the valve (52) from a first position to a second position at which the valve means (52) is stopped from further movement in said first direction. Further movement of the plunger (58) in said first direction causes the plunger (58) to slide relative to the valve (52). The device (10) is intended for treatment of Mënière's disease and ear pain from other causes.

A1

12 Claims, 10 Drawing Sheets

FOREIGN PATENT DOCUMENTS

| | | |
|---|---|---|
| FR | 2605516 | 4/1988 |
| WO | WO 83/02556 | 8/1983 |
| WO | WO 00/01331 | 1/2000 |
| WO | WO 00/01346 | 1/2000 |
| WO | WO 00/10484 | 3/2000 |
| WO | WO 01/19244 A1 | 3/2001 |

* cited by examiner

PORTABLE HAND-OPERABLE DEVICE FOR APPLYING PNEUMATIC PRESSURE PULSES TO AN EAR CANAL

The is application is the U.S. National Phase under U.S.C. §371 of International Application PCT/AU 2004/000655 filed on May 19, 2004, which claims priority of Australian Patent Application No. 2003902425 filed on May 19, 2003. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

FIELD OF THE INVENTION

The present invention is directed to a portable device that is useful for the treatment and/or alleviation of symptoms of various ear disorders. It is also directed to the use of such a device.

BACKGROUND OF THE INVENTION

Mënière's disease is a disorder of the inner ear. It is characterised by an endolymphatic hydrops of unknown cause. Symptoms consist of disturbed balance, vertigo, impaired hearing and tinnitus. It has been shown that people suffering from Mënière's disease can achieve relief from symptoms of dizziness and nausea through the application of elevated pressure to the outer and middle ear.

It is theorised that an air pulse, which applies the pressure to the round window of the inner ear may assist in reversing the flow of toxic potassium ions from the scala tympani to the scala vestibuli. The present invention provides a low cost device designed to allow users to apply elevated pressure levels to their own ears in order to achieve such relief.

The inventor has also recognised that causing a negative change of pressure in the ear canal may be useful in relieving pain arising from other causes, such as unequal pressure between the middle ear and outer ear that occurs during descent of an aircraft. The present invention also provides a device which may achieve such relief.

SUMMARY OF THE INVENTION

The present invention seeks to provide devices that are simple to operate to provide either a positive or negative change in pressure in the ear canal. The invention also seeks to provide such devices that are portable and hand-operable. The device can therefore be carried by a person and easily used, without the assistance of additional mains or battery electric power, whenever relief is sought from various disorders of the ear.

Accordingly, in a first embodiment the present invention is directed to a hand-held and hand-operable device for creating a change in pressure in an external ear canal of a person, said device comprising:
- a body having an interior space forming an air chamber;
- within the air chamber, a plunger and a valve means frictionally engaged with said plunger;
- a flexible tube in fluid communication at a first of its ends with said air chamber and, at the second of its ends, with an ear-piece adapted for insertion in said ear canal;
- a finger-actuated diaphragm in an external wall of the air chamber which:
   when depressed by a user's finger, moves the plunger from a resting position, and in a first direction, and when released by the user's finger, returns to its undepressed position; and
- a spring means for returning the plunger, in a second direction, to said resting position when said finger depression on the diaphragm is removed;

wherein:
  initial movement of the plunger in said first direction from said resting position displaces said valve means from a first position to a second position at which the valve means is stopped from further movement in said first direction,
  further movement of the plunger in said first direction causes the plunger to slide relative to the valve means,
  initial said return movement of the plunger in said second direction displaces said valve means from said second position to said first position at which the valve means is stopped from further movement in said second direction,
  further movement of the plunger in said second direction causes the plunger to slide relative to the valve means, and
  either:
    said depression of the diaphragm increases the pressure of the air in said air chamber, or
    said return of the diaphragm to its undepressed position decreases the pressure of the air in said air chamber, whereby, when the ear-piece is inserted in said ear canal, actuation of the diaphragm causes said increase or decrease of air pressure, generated at the air chamber, to be transmitted through the tube and delivered to the ear canal.

The valve means may include a cylindrical valve stem which engages in a close sliding fit within a bore in the plunger and said close sliding fit provides said frictional engagement. The plunger may slide axially in a cylindrical chamber formed within said interior space.

The diaphragm preferably has a generally hat shape the crown of which accommodates an end of the plunger when in its said resting position.

In one embodiment the depression of the diaphragm may cause an increase of air pressure to be delivered to the ear canal. The valve means when at said second position may have its sealing face pressed against a co-operating port to prevent air flow through that port.

The valve means may include a cylindrical valve stem which is held in a loose sliding fit by a retainer affixed within the cylindrical chamber and, when the valve means is at said first position, the valve means is prevented by the retainer from further movement in said second direction.

In another embodiment the return of the diaphragm to its undepressed position causes a decrease of air pressure to be delivered to the ear canal. The valve means when at said first position may have its sealing face pressed against a co-operating port to prevent air flow through that port.

BRIEF DESCRIPTION OF THE DRAWINGS

The present invention shall now be described with reference to the following drawings which illustrate preferred embodiments of the invention. These drawings are merely illustrative of how the invention may be put into effect so that the specific form and arrangement of the various features as shown is not to be understood as limiting the invention.

DESCRIPTION OF THE PREFERRED EMBODIMENTS AND OTHER EXAMPLES OF THE INVENTION

Figure 1:
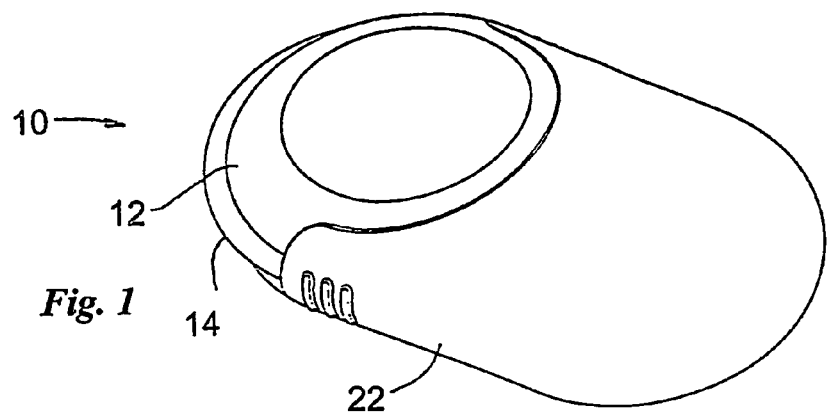
FIG. 1 is a perspective view of an air pulsing device according to a first embodiment of the present invention shown with its delivery tube wound onto its case and its cap in place as for storage or transport in a person's pocket.
Figure 2:
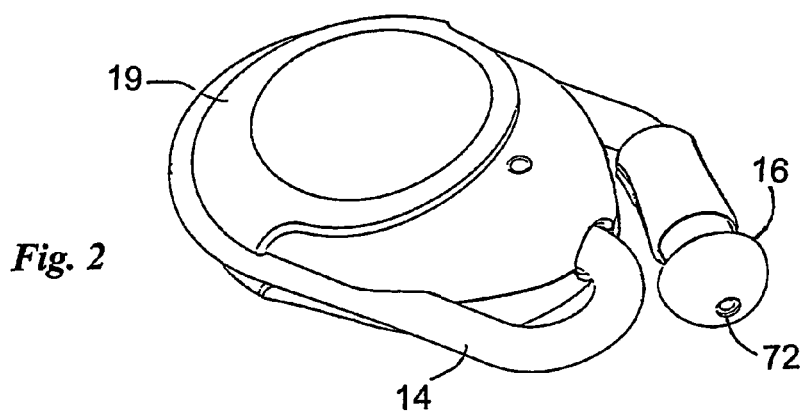
FIG. 2 is a view of the device in FIG. 1, shown with the storage cap removed.
Figure 3:
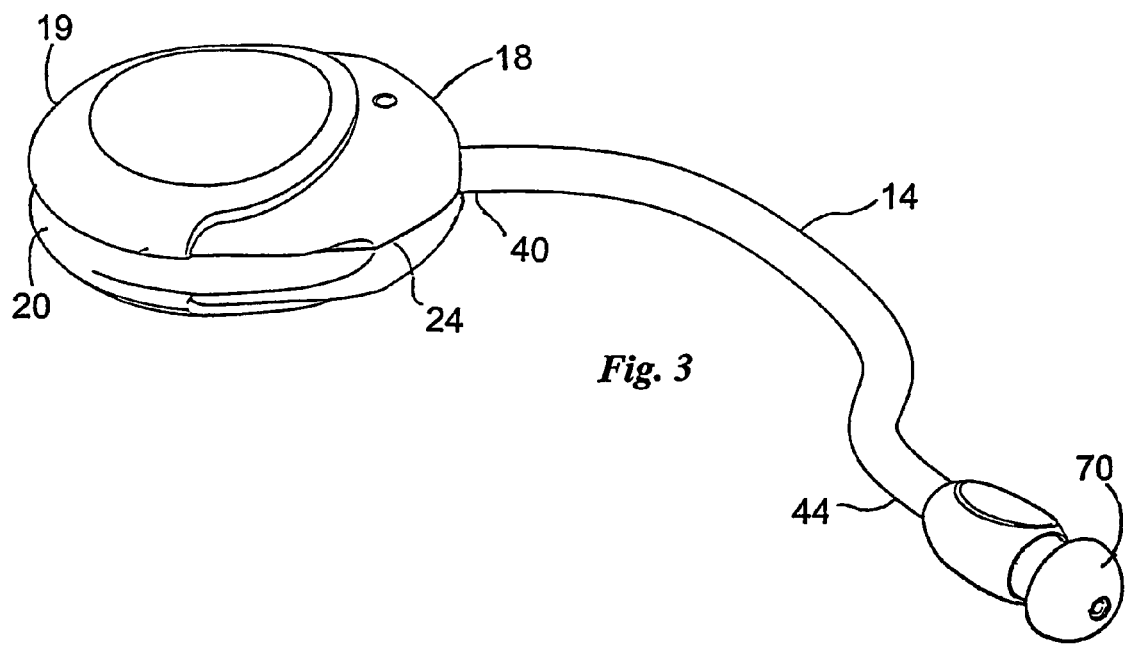
FIG. 3 is a perspective view of the device in FIG. 2 shown with the delivery tube unwound and ready for use.
Figure 4:
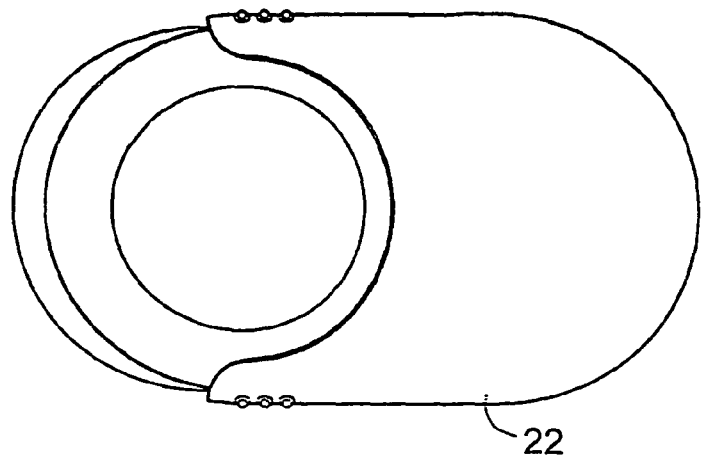
FIG. 4 is a top view of the device shown in FIG. 1.
Figure 5:
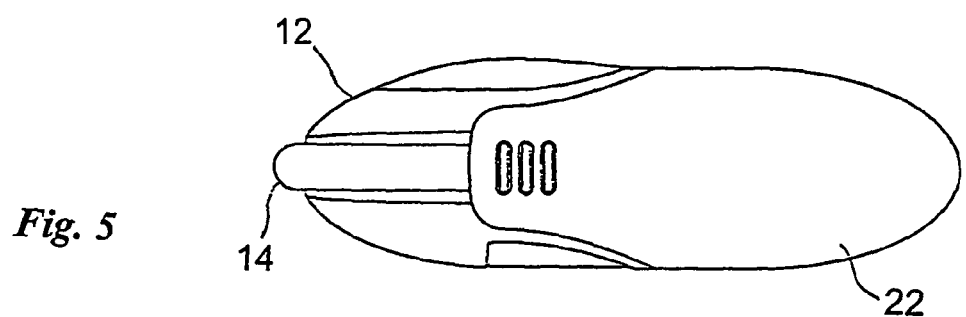
FIG. 5 is a side view of the device shown in FIG. 1.
Figure 6:
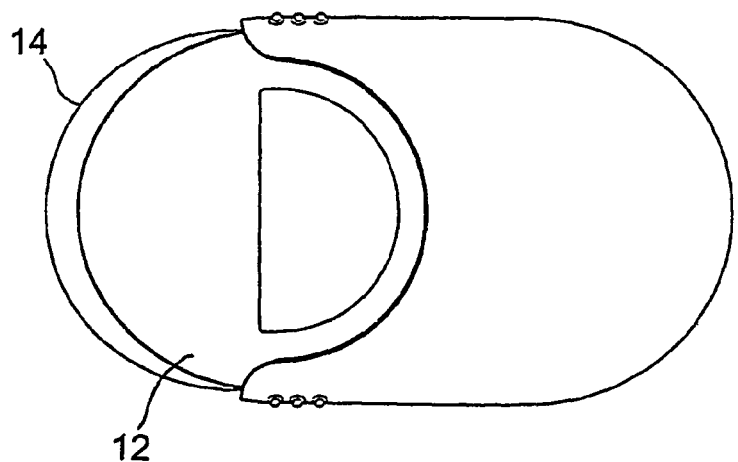
FIG. 6 is a bottom view of the device shown in FIG. 1.
Figure 7:
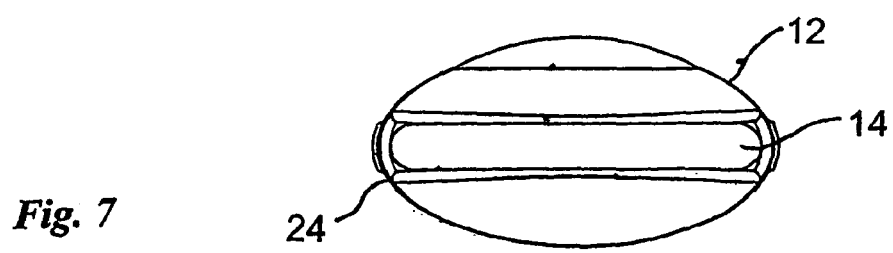
FIG. 7 is an end view of the device shown in FIG. 1.
Figure 8:
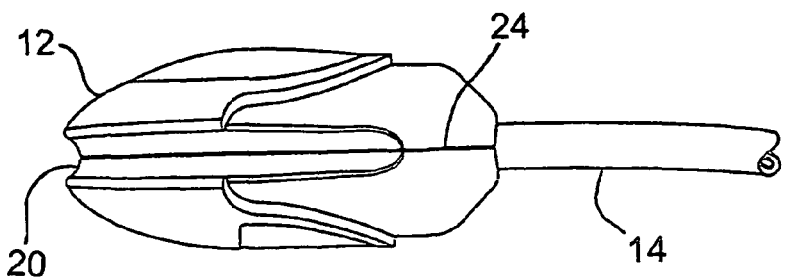
FIG. 8 is a side view of portion of the device as shown in FIG. 3.
Figure 9:
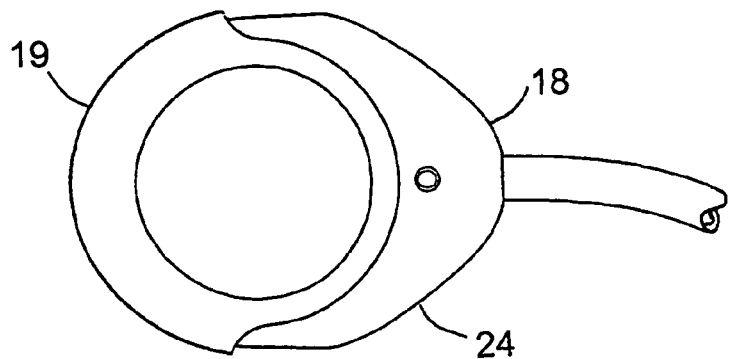
FIG. 9 is a top view of the portion of the device shown in FIG. 8.
Figure 10:
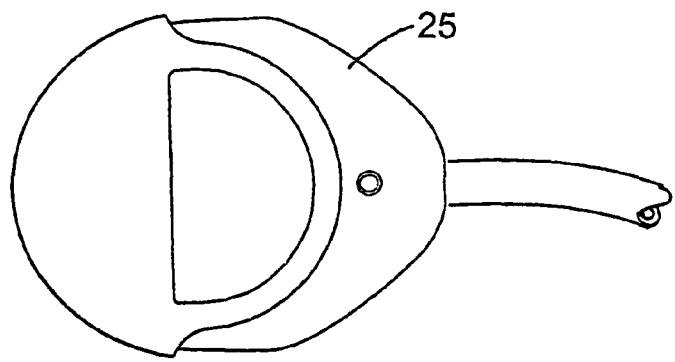
FIG. 10 is a bottom view of the portion of the device shown in FIG. 8.
Figure 11:
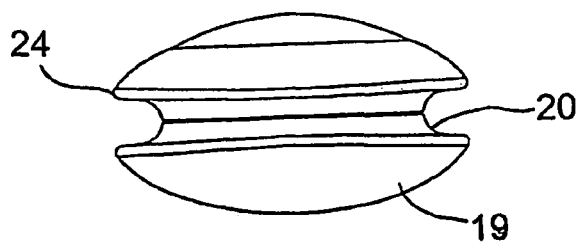
FIG. 11 is an end view of the portion of the device shown in FIG. 8.

Referring to FIGS. 1 to 14, the air-pulsing device 10 illustrated has a main body portion 12 to which is attached a flexible rubber tube 14 at the end of which is an ear piece 16 which in use is placed in the patient's ear. The main body portion 12 is about palm sized and has a generally squashed slightly-ellipsoidal form, so that it is somewhat discus-shaped, although slightly elongated, with a peripheral rim 24. At one of the elongated ends 18 of the body 12, the tube 14 extends from the rim 24. At the opposite end 19 of the body 12, a rounded groove 20 extends along the rim 24 and this serves as a locating recess for the tube 14 when it is wound into its storage position as shown in FIG. 2. The tube 14 wraps along the rim 24 of the body 12 for convenient storage. As shown in FIG. 1, an end cap 22 clips onto the end 18 of the body opposite the groove to cover and protect the ear piece 16 and the tube 14 where it extends from the body 12.

Figure 12:
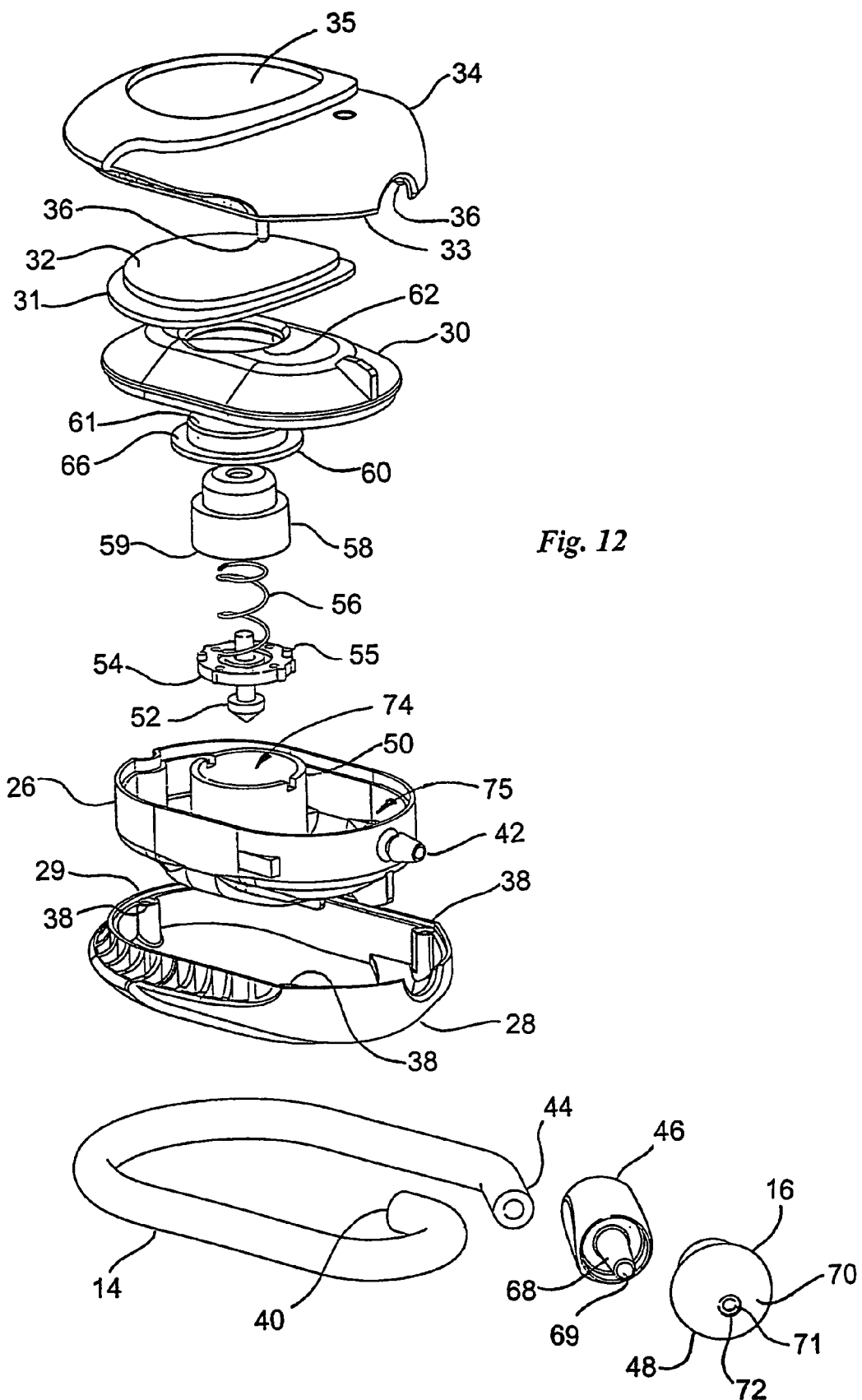
FIG. 12 is an exploded view of the device shown in FIG. 2.
Figure 13:
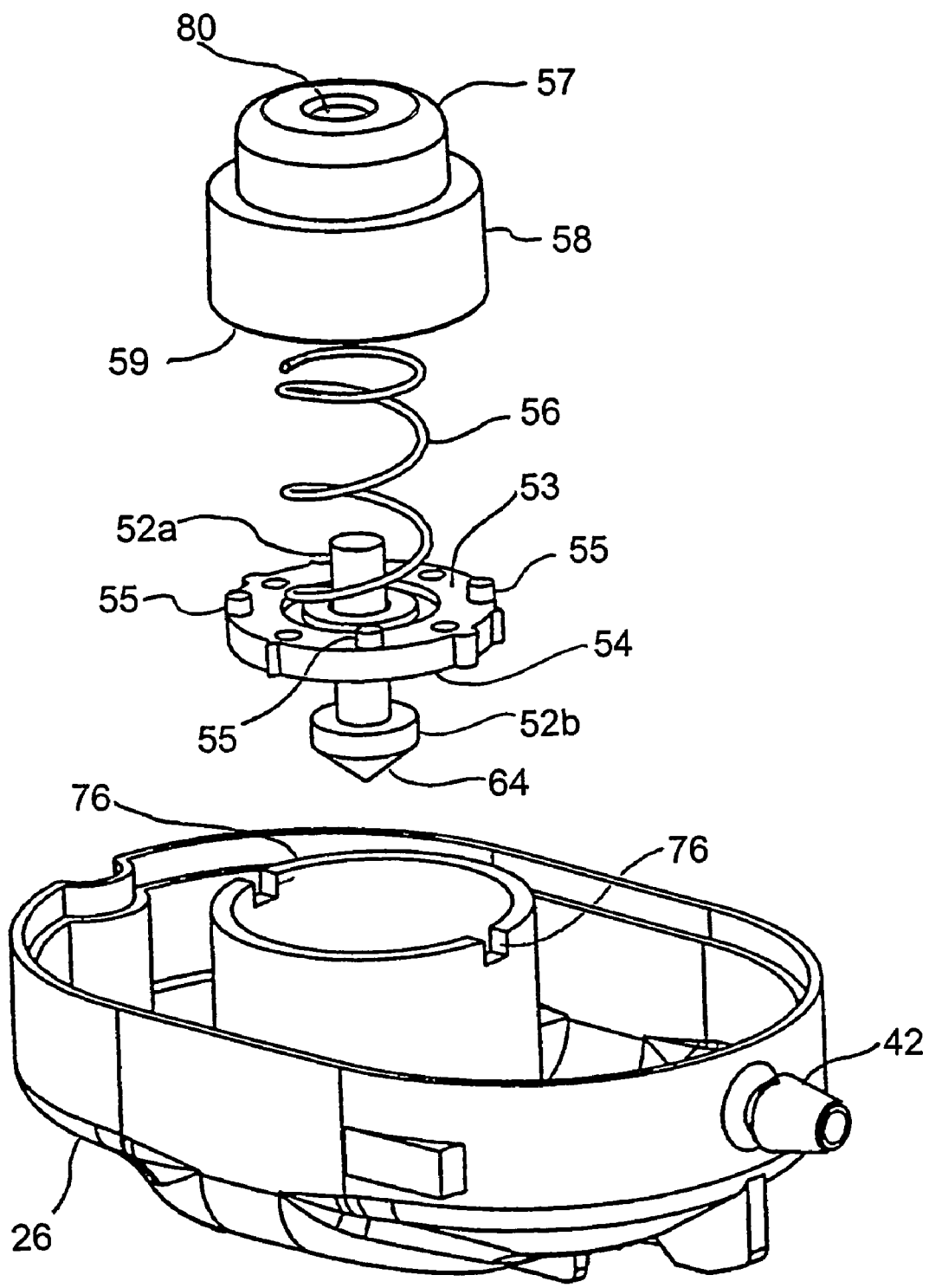
FIG. 13 is an enlargement of portion of the exploded view in FIG. 12.
Figure 14:
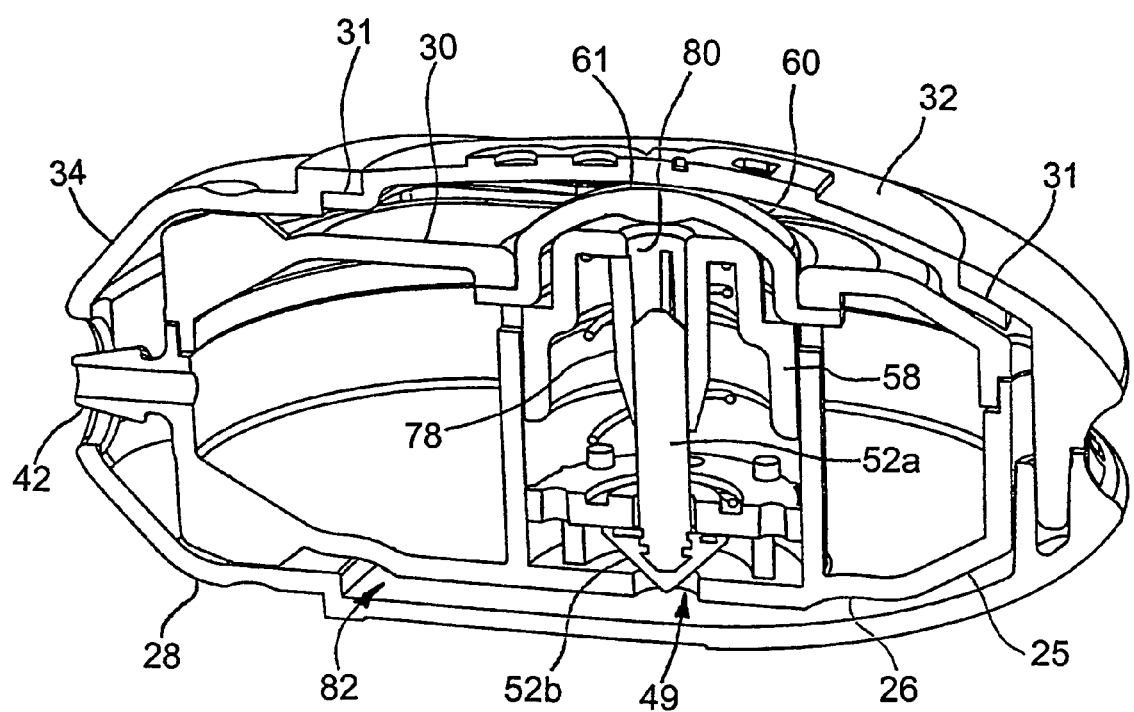
FIG. 14 is a cut-away perspective view of the device according to the first embodiment.

Referring in particular now to FIGS. 12 and 13, the main body portion 12 has a pressure case 25 formed by fastening together a pressure case base 26 and a pressure case top 30. The pressure case base 26 nests into a bottom cover 28. The pressure case top 30 is covered by a top cover 34 which has a large circular aperture 35 therethrough which is filled by an actuating pad 32. The rim 31 of the actuating pad 32 is glued to the top cover 34 and sandwiched between the pressure case top 30 and top cover 34.

The tube 14 is made from flexible silicone rubber and has one end 40 located onto a barbed nozzle 42 integrally formed on the pressure case base 26. The nozzle 42 provides a port into the pressure case 25. The second end 44 of the tube 14 is attached to an ear piece adaptor 46 onto which is located an ear piece 48.

The pressure case base 26 has integrally formed within it a cylindrical chamber or compartment 50 having its longitudinal axis aligned from base 26 to top 30, ie. perpendicular to the plane of the rim 24. Within the cylinder 50 is housed a needle valve 52 which has a cylindrical stem 52a and a softer, conical shaped tip 52b affixed to the bottom end of the stem 52a. The valve 52 is retained by a generally disc-shaped valve retainer 54. Also housed within the cylinder 50 is a plunger 58, which is biased away from the valve retainer 54 by a coil spring 56 in compression. The plunger is biased upwardly against a diaphragm 60 which covers and protrudes through a circular opening 62 in the pressure case top 30. The diaphragm 60 has the general shape of a hat, the crown 61 of which accommodates the upper end 57 of the plunger 58.

At the bottom 40 of the cylinder 50 is a central circular hole onto which the tapered sealing face 64 of the valve 52 seats. This hole provides a port 49 which opens from the cylinder 50 to the small gap 82 between the pressure case base 26 and the bottom cover 28. The port 49 is a simple parallel bore so that its hard upper edge seals against conical face 64 of the soft tip 52b of the valve 52.

The end cap 22, pressure case base 26, pressure case top 30, bottom cover 28, and plunger 58 are all made of a suitable engineering grade of rigid plastics material. The actuating pad 32 and pressure diaphragm 60 are made of flexible rubber.

To assemble the device 10, the pressure diaphragm 60 is first glued around its perimeter to the inside of the pressure case top 30, across the opening 62, in a manner to ensure a tight seal is achieved around the edge. The spring 56, valve 52, valve retainer 54 and plunger 58 are then positioned in the cylinder 50, and the pressure case top 30 and pressure case base 26 are glued together at their respective rims 33 and 29 being careful to ensure that the plunger, valve and spring are free to move axially in the cylinder 50.

The diaphragm 60 is a thin-walled rubber moulding which has an outwardly extending peripheral flange 66 which seals against the underside of the corresponding inner edge of the opening 62 in the pressure case top 30. The actuating pad 32 is glued into the top cover 34 and a small dob of glue is used to affix the top face of the pressure diaphragm 60 to the bottom face of the pad 32. The rim 29 of the bottom cover 28 is then affixed to the engaging rim 33 of the top cover 34. Locating pins 36 on the top cover (only two of which can be seen in FIG. 12) locate into corresponding holes 38 on the bottom cover 28 in order to ensure correct alignment of the rims 29 and 33.

The ear piece adaptor 46 has a barbed connection (hidden in Figures) by which it is affixed to the free end 44 of the tube 14. The ear piece 48 is removably connected to a protruding tapered nozzle 68 on the ear piece adaptor 46. While the connection between the adaptor 46 and the tube 14 is not intended to be separated, the ear piece 48 is readily removed for replacement.

The ear piece 48 has a dome-shaped outer end 70 and when placed in an ear canal, the end 70 forms a peripheral seal. The ear piece 48 has an axial bore 71 ending at an opening 72 in the outer end 70. It is desirable for proper treatment of a patient's condition that the ear piece 48 provides a good, generally airtight seal.

After assembly, if finger pressure is applied to the actuating pad 32, the diaphragm 60 is depressed, so reducing the volume of the air chamber 74 defined by the cylinder 50 and the diaphragm 60. Air is prevented from escaping through the bottom port 49 sealed by valve 52, so is expelled from the chamber 74 through a pair of rectangular ports 76 positioned at diametrically opposite sides of the top edge of cylinder 50.

The amount of air expelled is controlled by the distance which the diaphragm 60 can be depressed. Maximum depression occurs when the bottom rim 59 of the plunger 58 contacts the upper surface of the valve retainer 54 and the sealing face 64 of the valve is pressed hard against its co-operating port.

To allow for the manufacture of devices which vary only in the displacement the plunger is allowed, four pins 55 are moulded on the upper face 53 of the valve retainer 54. The height of these pins may be conveniently adjusted in the tooling used to mould the retainer 54. The longer the pins are the lower the air pressure produced by the device.

Users of the device 10 to treat Mënière's Disease will either have a ruptured eardrum or a tympanostomy tube fitted so that equal pressures are achieved either side of the eardrum. Therefore the volume into which the device 10 operates includes the middle ear connected cavities. The device 10 will produce safe pressure levels regardless of whether the user has an intact eardrum or not.

The device generates an elevated pressure change when the user presses the actuating pad 32 which in turn depresses the diaphragm 60. By fully actuating the diaphragm the chamber volume of the main body portion 12 is decreased by a fixed volume, resulting in a pressure increase in both the chamber and the user's ear cavity. The user may also elect to partially actuate the device in order to elevate ear pressure by a smaller amount.

The pressure elevation is determined by the ratio of starting combined device and ear cavity volume to the combined volume following actuation, as well as the atmospheric pressure.

To avoid damaging an ear, it is important that a safe maximum pressure and safe minimum pressure are never exceeded when using such a device. A maximum allowable pressure is 350 dapa (decapascals) above ambient pressure. Maximum pressure is defined by a maximum volumetric displacement of the pressure diaphragm into a minimum user ear canal volume. The device 10 is designed such that the pressure elevation when used in a 7 ml ear cavity is 215 dapa±40 above ambient pressure and the maximum possible negative pressure is 20 dapa below ambient. It is important that a negative pressure beyond 100 daPa below ambient pressure is not possible with the device A user ear canal volume of 0 ml is assumed in determining the maximum pressure to which a user could be exposed. This is equivalent to application to a user's ear with an intact eardrum and wax filled outer ear.

To prevent the device from producing a significant negative pressure, a friction-controlled valve is used. This valve is closed within the first millimetre or two of movement of the diaphragm as it is pressed, thereby sealing the device. As the diaphragm is further depressed the pressure within the device and connected user ear cavity is elevated.

When the user presses the diaphragm, the plunger is pressed downwards. The valve stem is frictionally engaged with the bore 80 in the plunger and freely runs through the bore of the retainer 54, so the valve seals port 49 very quickly. Thereafter the plunger is pressed downwards, its bore sliding on the valve stem, until its bottom rim 59 engages the retainer 54 at which time the internal operating volume of the device is at its minimum.

When the user begins to release the diaphragm, the plunger is pushed upwards by the spring 56 and the valve 52 is drawn upwards by means of the frictional engagement between the valve stem 52a and the bore 80 in the plunger, so the port 49 opens. This releases any pressure from the device and the user's ear cavity, allowing them to return to atmospheric pressure. The port will open within approximately the first millimetre of diaphragm relaxation from any level of diaphragm compression.

Negative gauge pressures are likely to cause additional discomfort to the user and are therefore to be avoided. If valve sequencing of the type described was not present, then it would be possible for the device to generate negative gauge pressures in a users' ear cavity under the following scenario:

the diaphragm is depressed whilst the device connected to a user's ear;
the seal to the outer ear is broken before the diaphragm is released thereby allowing the ear and device cavities to return to atmospheric pressure;
following full, or even partial equalization, the seal to the ear is reestablished;
the device diaphragm is released thereby increasing the effective cavity volume and reducing the pressure relative to the chamber pressure.

Turning now to the second embodiment of the invention illustrated in FIGS. 15 to 21, many of the components are the same configuration as those described above in relation to the first embodiment and so do not need to be described in detail again. Such components are the bottom cover 28, top cover 34, actuating pad 32, pressure case top 30, diaphragm 60, tube 14, ear piece adaptor 46 and ear piece 16.

From the outside, device 10 of the first embodiment and device 110 of the second embodiment look the same. But whereas the device 10 is used to produce a positive pressure in the ear canal, device 110 is used to produce a negative pressure. This requires a different valving arrangement but many of the same valve sequencing principles apply.

Figure 15:
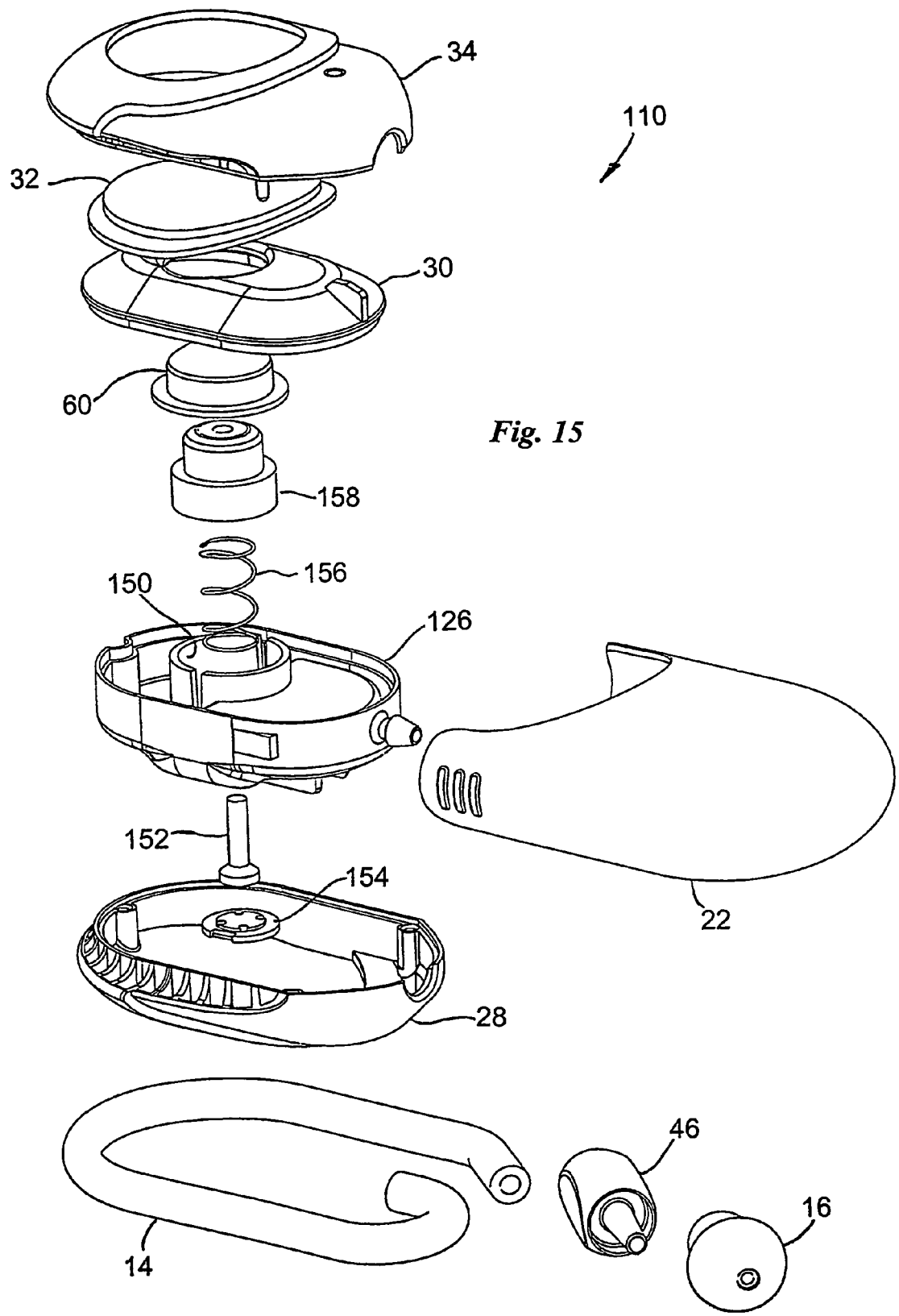
FIG. 15 is an exploded view of an air pulsing device according to a second embodiment of the present invention.
Figure 16:
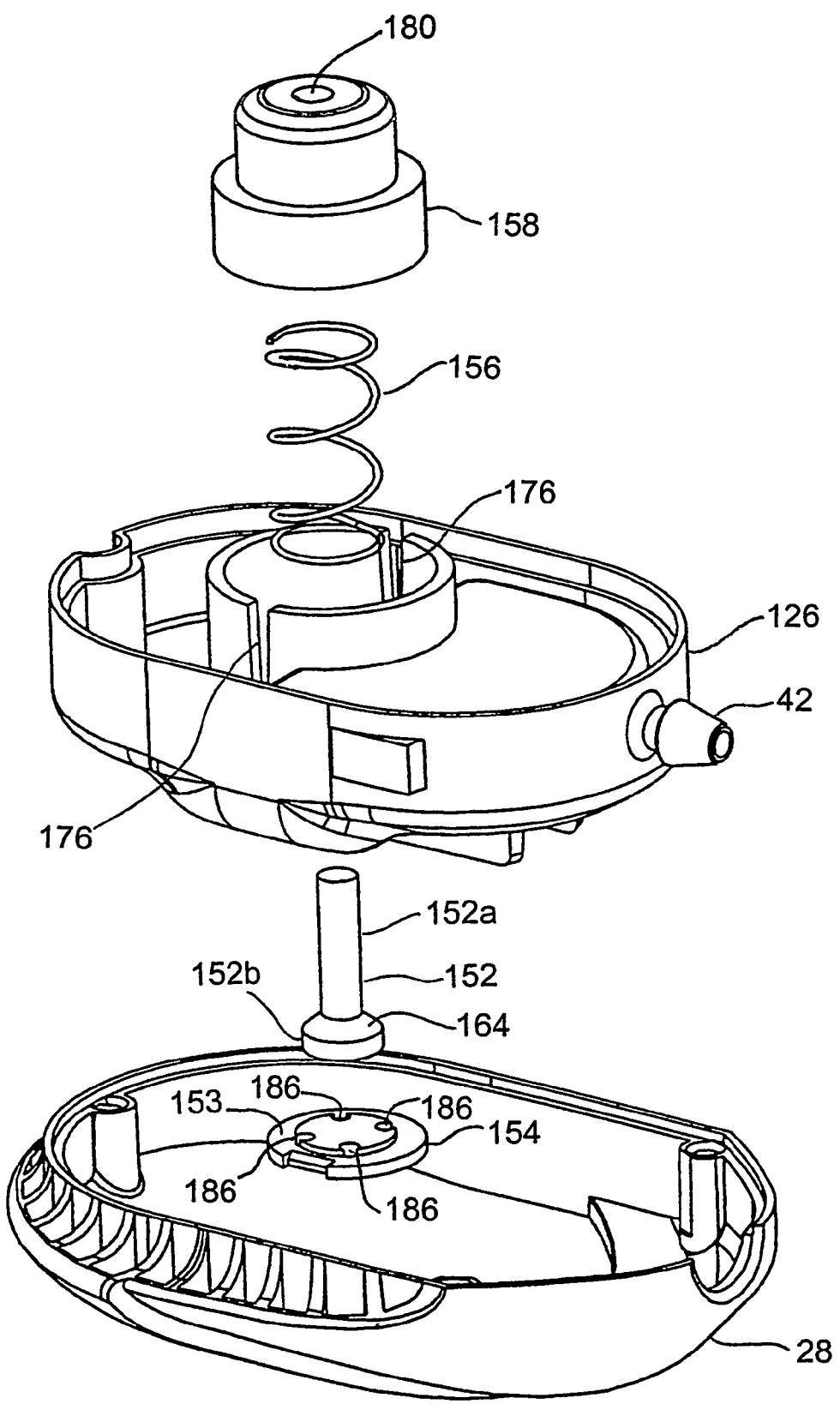
FIG. 16 is a detailed enlargement of portion of the exploded view in FIG. 15.

Referring now to FIGS. 15 and 16, the main body portion 112 has a pressure case 125 formed by fastening together a pressure case base 126 and a pressure case top 130, which is the same as top 30.

The pressure case 126 has integrally formed within it a cylindrical chamber or compartment 150. Whereas the device 10 had a needle valve which opened inwardly of the device, the device 110 of the second embodiment has a poppet valve 152 which opens outwardly of the pressure case 125. The poppet valve 152 and pressure case base 126 are assembled with the cylindrical valve stem 152a extending into the cylinder 150 along the longitudinal axis. A port 149 at the centre of the bottom of the cylinder 150 co-operates with the head 152b of the valve 152 to seal the port 149 when the valve 152 is in its upward most position.

Below the port 149 is a larger diameter aperture 147 through which the whole of valve 152 is fed upon assembly. A stop plate 154 is glued into position to blank off aperture 147. In its lower-most position the valve head 152 comes into contact with the stop plate 154.

The bottom wall 184 of the cylinder 150 is raised compared with the equivalent bottom wall in the earlier described embodiment and that raised wall contains the port 149 which is opened and shut by the valve 154. The valve stem 152a is inserted upwardly through the port 149 into the cylinder and the stop plate 154 then placed to fill the aperture 147. The bore 180 in the plunger 158 frictionally engages the valve stem 152a. A coil spring 156 is maintained in compression extending between the bottom wall of the cylinder and the plunger.

Figure 17:
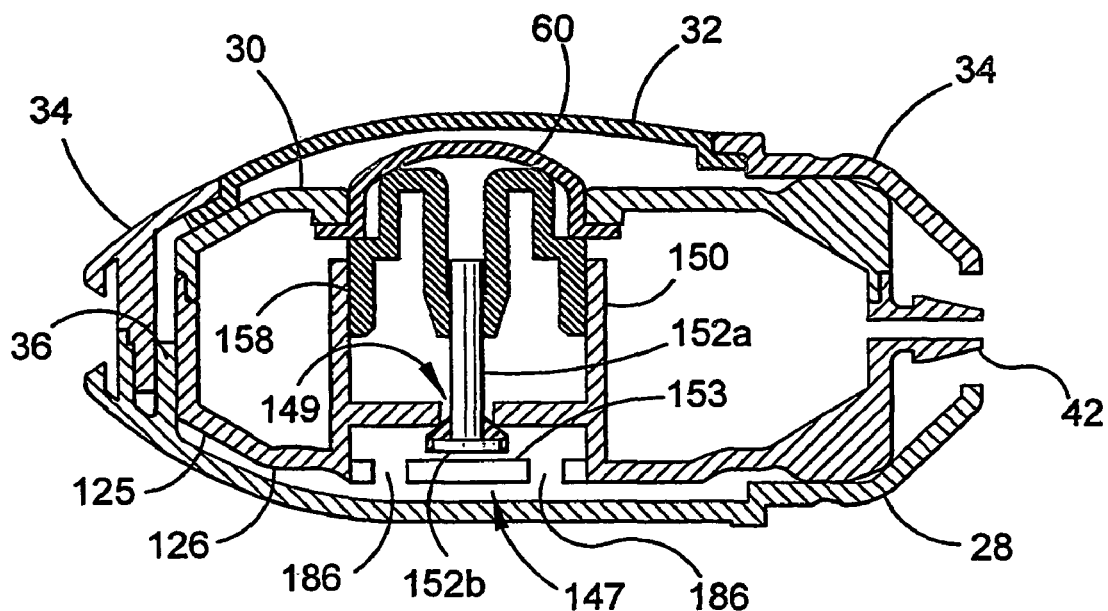
FIGS. 17 to 21 are cut away views showing the sequence of operations when using the device according to the second embodiment.

As illustrated in FIG. 17, the device 110 is static and ready for first use. The valve head 152b is sealed against the port 149.

Figure 18:
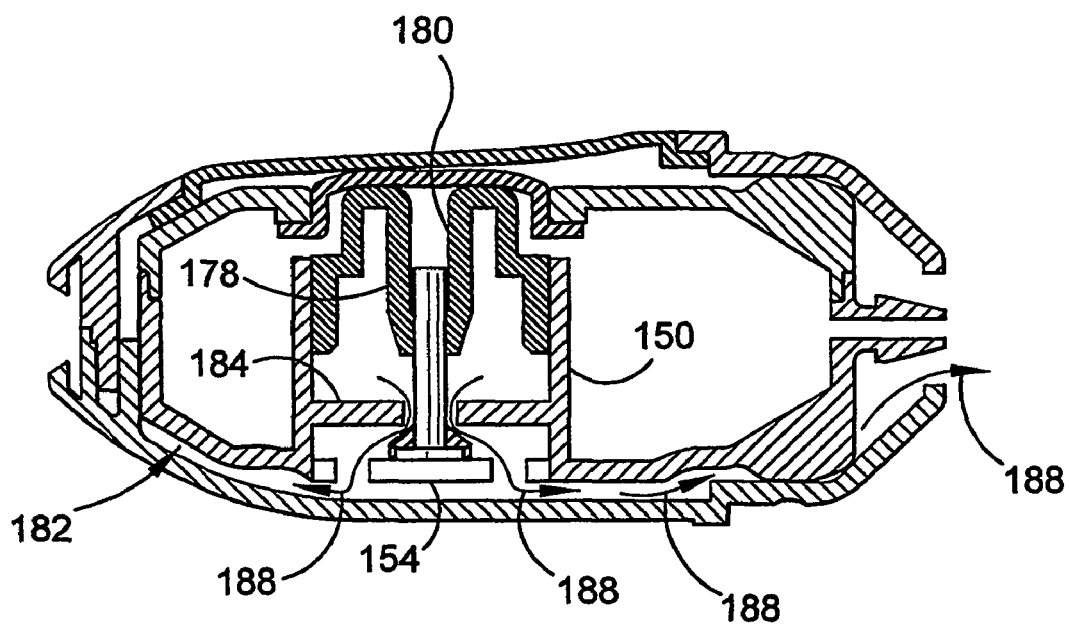

As seen in FIG. 18, initial depression of the actuating pad 132 causes the diaphragm 60 to move downwards slightly which in turn presses down the plunger 158. The valve stem 152a is frictionally held within the bore 180 of a socket feature 178 moulded on the inside of the plunger 158. So, as the plunger first moves downwards, the valve 152 opens the port 149 allowing air to flow through the port, then through apertures 186 in the stopper plate and out to atmosphere through the space 182 between the bottom cover 128 and pressure case base 126 and through a gap between the fixed end 40 of the tube and the surrounding covers 28 and 34. This flow of air is shown by the arrows 188 shown in FIG. 18. The valve head 152b has just come into contact with the stopper plate and the valve stem has not yet slipped from its friction grip in the bore 180.

Figure 19:
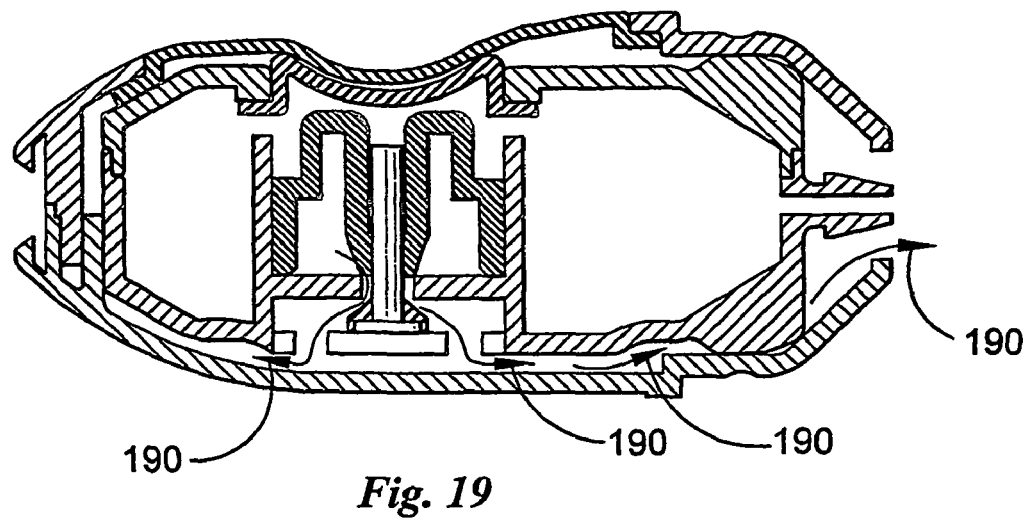

FIG. 19 shows the device at the point of full actuation. The valve head has remained in contact with the stopper plate and the plunger has slid down the valve stem 152a, the finger pressure from the user having overcome the friction between the bore 180 and the valve stem. The air flow to atmosphere is shown by arrows 190. In FIG. 19 the plunger is shown fully depressed so the system is at its minimum volume. At this stage the device still has atmospheric pressure within it.

Figure 20:
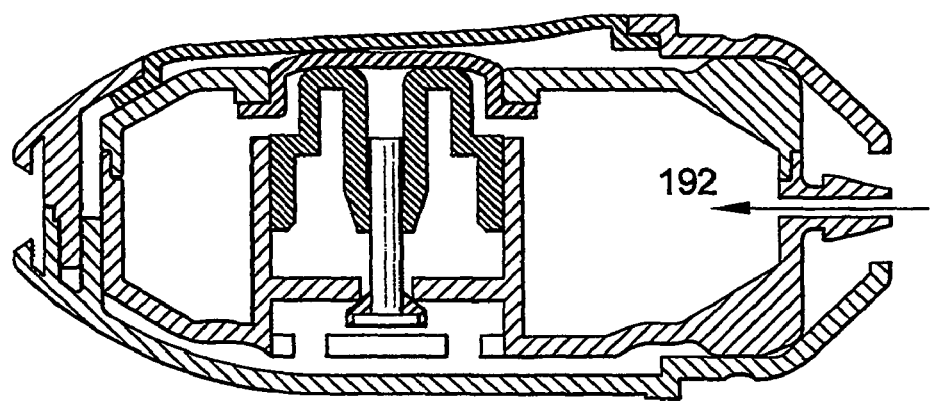

Referring now to FIG. 20, the diaphragm has been partly released and the plunger has risen under action from the spring bringing with it, by frictional engagement, the valve. After about 1 mm movement, the valve head seals the port. At this point the plunger starts to slip on the stem of the valve. The device is still at atmospheric pressure internally.

As the plunger continues to rise, the volume of the system increases and the pressure drops, drawing air along the tube 14 as shown by arrow 192.

Figure 21:
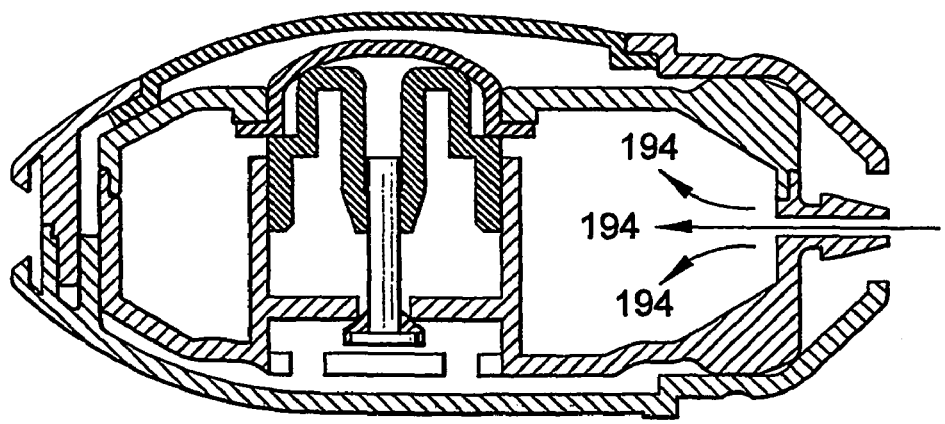

As shown in FIG. 21 the plunger has continued to rise, with the valve stem sliding in the bore 180 of the plunger, further increasing the volume, drawing further air into the device and lowering the pressure further.

At the position shown in FIG. 21, maximum negative pressure is achieved in the system and the pressure will hold until the seal is broken or the diaphragm is pushed again.

When the user begins to press the diaphragm again, the valve opens. This releases any negative pressure within the device and the user's ear cavity, allowing them to return to atmospheric pressure.

It is important to note that the plunger does not act as a piston in the cylinder. Air flows are produced by actuation of the diaphragm which increases and decreases the total volume of the air chamber in the device. As seen in FIG. 16 the cylinder has longitudinal slits 176 through its walls which allows free air flow between the piston and the main part of the body of the device.

It can be seen that the device generates a pressure reduction relative to atmospheric pressure when the user squeezes and releases a diaphragm. By actuating the diaphragm, the effective volume of the device is decreased by a fixed volume. When the diaphragm is released a valve seals the chamber port to atmosphere and the chamber size increases resulting in a reduced pressure in both the chamber and the user's ear cavity. The user may also elect to partially actuate the device in order to reduce the air pressure by a smaller amount than the maximum provided by the design of the device.

The friction-controlled valve is used to prevent the device from producing a significant positive pressure between actuations. This valve is closed within the first millimetre of movement when the diaphragm is released, thereby sealing the operating cavity from venting to atmosphere. As the diaphragm is further released the pressure within the operating cavity and connected user ear cavity is reduced.

The valve will open within approximately the first millimetre of diaphragm actuation from any level of diaphragm compression.

If this type of valve was not present then it would be possible for the device to generate positive gauge pressures in a users' ear cavity under certain conditions of poor sealing to the user's ear, such as when the seal is broken during actuation and then re-established.

For patient safety, it is important that excessive negative and positive pressures cannot be exceeded under any circumstances of using this device. For the above described second embodiment of the invention, the minimum actuation pressure (maximum amplitude) allowable is 700 dapa gauge (below ambient). The design gives a holding actuation gauge pressure of −500 dapa with a tolerance of +/−40 dapa gauge for normal usage at a nominal ear cavity size of 2 ml and an atmospheric pressure of 10132500 daPa. Also it is important that a device of this type cannot be used to create a positive pressure greater than 100 dapa above ambient pressure under conditions of effective and/or ineffective sealing to the ear.

Whilst the above description includes the preferred embodiments of the invention, it is to be understood that many variations, alterations, modifications and/or additions may be introduced into the constructions and arrangements of parts previously described without departing from the essential features or the spirit or ambit of the invention.

It will be also understood that where the word "comprise", and variations such as "comprises" and "comprising", are used in this specification, unless the context requires otherwise such use is intended to imply the inclusion of a stated feature or features but is not to be taken as excluding the presence of other feature or features.

The invention claimed is:

1. A hand-held and hand-operable device for creating a change in pressure in an external ear canal of a person, said device comprising:
 a body having an interior space forming an air chamber;
 within the air chamber, a plunger and a valve means frictionally engaged with said plunger;
 a flexible tube in fluid communication at a first of its ends with said air chamber and, at the second of its ends, with an ear-piece adapted for insertion in said ear canal;
 a finger-actuated diaphragm in an external wall of the air chamber which:
  when depressed by a user's finger, moves the plunger from a resting position, and in a first direction, and
  when released by the user's finger, returns to its undepressed position; and
 a spring means for returning the plunger, in a second direction, to said resting position when said finger depression on the diaphragm is removed;
wherein:
 initial movement of the plunger in said first direction from said resting position displaces said valve means from a first position to a second position at which the valve means is stopped from further movement in said first direction,
 further movement of the plunger in said first direction causes the plunger to slide relative to the valve means,
 initial said return movement of the plunger in said second direction displaces said valve means from said second position to said first position at which the valve means is stopped from further movement in said second direction,
 further movement of the plunger in said second direction causes the plunger to slide relative to the valve means, and
either:
 said depression of the diaphragm increases the pressure of the air in said air chamber, or said return of the diaphragm to its undepressed position decreases the pressure of the air in said air chamber, whereby, when the ear-piece is inserted in said ear canal, actuation of the diaphragm causes said increase or decrease of air pressure, generated at the air chamber, to be transmitted through the tube and delivered to the ear canal.

2. The device of claim 1, wherein the valve means includes a cylindrical valve stem which engages in a close sliding fit within a bore in the plunger and said close sliding fit provides said frictional engagement.

3. The device of claim 1, wherein the plunger slides axially in a cylindrical chamber formed within said interior space.

4. The device of claim 1, wherein the diaphragm has a generally hat shape; the crown of which accommodates an end of the plunger when in its said resting position.

5. The device of claim 1, wherein said depression of the diaphragm causes an increase of air pressure to be delivered to the ear canal.

6. The device of claim 5, wherein the valve means when at said second position has its sealing face pressed against a co-operating port to prevent air flow through that port.

7. The device of claim 5 wherein the valve means includes a cylindrical valve stem which is held in a loose sliding fit by a retainer affixed within the cylindrical chamber and, when the valve means is at said first position, the valve means is prevented by the retainer from further movement in said second direction.

8. The device of claim 7, wherein a coil spring extending between the plunger and the retainer is maintained in compression in order to maintain a thrust pressing the plunger away from the retainer.

9. The device of claim 1, wherein said return of the diaphragm to its undepressed position causes a decrease of air pressure to be delivered to the ear canal.

10. The device of claim 9, wherein the valve means when at said first position has its sealing face pressed against a co-operating port to prevent air flow through that port.

11. The device of claim 6, wherein the valve means includes a cylindrical valve stem which is held in a loose sliding fit by a retainer affixed within the cylindrical chamber and, when the valve means is at said first position, the valve means is prevented by the retainer from further movement in said second direction.

12. The device of claim 11, wherein a coil spring extending between the plunger and the retainer is maintained in compression in order to maintain a thrust pressing the plunger away from the retainer.

* * * * *